United States Patent [19]

Mares et al.

[11] 4,286,068

[45] Aug. 25, 1981

[54] CATALYST AND PROCESS FOR OXIDATION OF ORGANIC SUBSTRATES BY HYDROGEN PEROXIDE

[75] Inventors: Frank Mares, Whippany; Stephen E. Jacobson, Succasunna, both of N.J.

[73] Assignee: Allied Chemical Corporation, Morris Township, Morris Co., N.J.

[21] Appl. No.: 144,073

[22] Filed: Apr. 28, 1980

Related U.S. Application Data

[63] Continuation of Ser. No. 929,376, Jul. 31, 1978, abandoned.

[51] Int. Cl.³ .............................................. C08J 9/36
[52] U.S. Cl. ................................. 521/53; 260/343.5; 260/348.23; 260/348.31; 521/56; 521/139; 521/140; 521/147; 560/131; 560/231; 562/503; 562/508
[58] Field of Search ................. 521/140, 56, 53, 139, 521/147; 260/343.5, 348.23, 348.31; 560/231; 562/503, 508

[56] References Cited

U.S. PATENT DOCUMENTS

| | | | |
|---|---|---|---|
| 3,993,673 | 11/1976 | McMullen | 260/348.5 L |
| 4,045,493 | 8/1977 | Trevillyan | 260/604 HF |
| 4,098,973 | 7/1978 | Smith | 526/21 |

FOREIGN PATENT DOCUMENTS 44-10243 of 1969 Japan.
45-2728 of 1970 Japan.

OTHER PUBLICATIONS

Talanta (1), vol. 17 of 1970, pp. 483–489.
Talanta (2), vol. 23 of 1976, pp. 590–593.
Angewandte Chemie, vol. 16 of 1977, pp. 493–558 (Int. Ed.).

*Primary Examiner*—Morton Foelak
*Attorney, Agent, or Firm*—Alan M. Doernberg; Gerhard H. Fuchs

[57] ABSTRACT

A process for oxidizing organic substrates such as ketones and ethylenically unsaturated compounds. The substrate is contacted with aqueous hydrogen peroxide in a solution or in a two-phase liquid system, in the presence of a polymeric catalyst containing chemically bonded arsenic. This process can lead to lactones or hydroxy acids from cyclic ketones or to esters or mixtures of alcohol and carboxylic acid from open chain ketones. Unsaturated compounds afford epoxides and/or diols. Preparations of certain polymers substituted by arsenic groups, particularly from polystyrene, poly(vinylpyridine) and copolymers thereof, useful as catalysts in such oxidation process, are described. For example, polystyrene is brominated, bromine therein is replaced by lithium and the resulting lithiated polymer is converted into a polymer containing an arsenic group, such as arsono, $-As(O)(OH)_2$, as substituent group, by reaction with arsine triethoxide followed by oxidation and hydrolysis by aqueous hydrogen peroxide. The aromatic polymers, polyphenylene and polymers and copolymers of vinylpyridine, can be used similarly as the catalyst.

6 Claims, No Drawings

CATALYST AND PROCESS FOR OXIDATION OF ORGANIC SUBSTRATES BY HYDROGEN PEROXIDE

This is a continuation, of application Ser. No. 929,376, filed July 31, 1978 and now standing abandoned.

BACKGROUND OF THE INVENTION

Cyclic ketones are oxidized to lactones or hydroxy acids with peracids in the Baeyer-Villiger reaction. Such peracids include persulfuric, perbenzoic, perphthalic, peracetic and trifluoroperacetic acid. In some instances peracids can be substituted by concentrated (90%) $H_2O_2$ and carboxylic acid anhydride.

S. Kamimura et al. in Japan Patent Publication No. 10243-1969 issued May 13, 1969 disclose a method for making esters including cyclic esters, i.e. lactones, by oxidation of ketones including substituted saturated and unsaturated cyclic ketones and alkyl aryl ketones, with hydrogen peroxide in the presence of arsenic, and in general, organic and inorganic arsenic compounds as catalysts. Desirably the ketone contains the structure $—CH_2CO—$; and the arsenical catalyst is an arsenate, arsenite or arsenic oxide soluble in the reaction solvent.

S. Kamimura et al. in Japan Patent Publication No. 2728/1970 dated Jan. 29, 1970 discloses a method for making 6-hydroxycaproic acid or its cyclohexylester by decomposition of cyclohexanone peroxides in the presence of arsenic or an arsenic compound as catalyst. A variety of arsenic compounds is proposed, such as oxides, halides and sulfides; and simple organic compounds of arsenic. Use of a solvent stable under the reaction conditions is said to be desirable; a number of specific solvents are named.

In generally similar manner, it is known to oxidize olefins to epoxides by use of arsenic or an arsenic compound as catalyst (U.S. Pat. No. 3,993,673 of Nov. 23, 1976 to McMullen).

To us it seemed possibly desirable to substitute, for the arsenic compounds proposed by Kamimura et al., and by McMullen, polymeric compounds substituted by arsenic groups in porous solid form such as porous granules or beads. Thereby an easy and complete separation of the product mixture in liquid form from such solid granules or beads of arsenical catalyst might be obtainable e.g. by filtration; provided that the polymer, substituted by arsenic groups, is highly stable to the oxidizing reaction conditions employed and sufficiently adsorptive toward the oxidation reaction mixture to achieve good contact of the reaction mixture with the catalytic sites. Accordingly, the polymer must be sufficiently inert and rugged, when in contact with the oxidation reaction mixture, to be resistant to the reaction mixture and easily separated therefrom and not be abraded, or dissolved, or decomposed, or converted into a soft, pulpy gel difficult to separate from the liquid reaction mixture; and at the same time, the polymer must allow ready access of the reaction mixture within the polymer.

Certain macroporous bead polymers substituted by arsenic groups have been studied for purposes of concentration and separation of trace metals from aqueous solutions such as sea water. One of these, polystyrene crosslinked with divinylbenzene ("DVB") and substituted in some of the phenyl rings by arsono (—As(O)(OH)$_2$) groups, appeared to us to be of possible interest for our purpose if it could be prepared with improved stability, toward oxidation by $H_2O_2$, over the product of the prior art. The prior art product from crosslinked polystyrene contained substantial amounts of nitrogenous and oxygen-containing substituents on the aromatic ring, such as azo and amino groups and also phenolate, which would be reactive with hydrogen peroxide. Such prior art is represented by the literature article of R. F. Hirsch et al. (Talanta vol. 17 of 1970, pages 483–489; polymer analysis at 486); and article of J. S. Fritz et al. (Talanta vol. 23 of 1976; pages 590–593) wherein use of three macroporous polystyrene DVB resins of differing average pore diameters and surface areas is described, each substituted by arsono groups by the general method of Hirsch, above noted (involving diazotization followed by coupling with sodium arsenite).

A possible alternative preparation might be by bromination and lithiation along the lines proposed in U.S. Pat. No. 3,998,864 of Dec. 21, 1976 to A. E. Trevillyan and divisional U.S. Pat. No. 4,045,493 (preparation of polyphenylene substituted by diphenylphosphine). In our case lithiation might allow introduction of arsenic groups; however we are not aware of any such disclosure in the prior art.

SUMMARY OF THE INVENTION

It is a principal purpose of the invention to provide an improved catalyst in the form of a polymer substituted by arsenic groups, useful for oxidation of a dissolved organic substrate by hydrogen peroxide, e.g. oxidation of dissolved ketones and ethylenically unsaturated compounds.

It is another purpose of the invention to provide such catalyst wherein any toxic elements are incorporated in a porous solid polymer so that the catalyst in granular or bead form can be easily separated from the reaction products in liquid form, and the toxic elements of the catalyst can be contained in the reactor and will not leak into the environment; while the porosity allows access of the oxidation reaction mixture to the catalytic sites.

It is another purpose of the invention to provide an arsenical catalyst which is highly stable toward $H_2O_2$ under oxidation reaction conditions.

It is another purpose of the invention to provide an arsenical catalyst, for oxidation purposes, which is safe in handling.

In accordance with this invention, an improved porous polymer in granular or bead form, substituted by arsenic groups and useful for catalyzing oxidation by hydrogen peroxide of e.g. ketones and ethylenically unsaturated compounds is provided, consisting essentially of phenyl or pyridyl groups, at least some of which are substituted on the ring by arsenic groups; being linked together in polyphenylene, or pendant from a polymethylenic backbone which is crosslinked by a divinylarylene; said polymer being free of nitrogenous and oxygen-containing substituents on the aromatic rings and thereby being highly stable toward $H_2O_2$. Especially such polymers having phenyl groups pendant from alternating methylenic carbon atoms derived from macroporous crosslinked polystryrene/DVB are of interest, for reasons of economy and effectiveness. Other starting materials from which to derive polymers, substituted by arsenic groups, in accordance with this invention are crosslinked polyvinylpyridine, crosslinked styrene/vinylpyridine copolymers, and polyphenylene. Under conditions requiring very high oxidative stability, a crosslinked styrene or vinylpyridine polymer fluorinated on the polymer backbone can be used as the starting material. Also such starting materials with ring substituents stable to oxidation, such as chlorine or bromine, can be used.

We have found a process for obtaining the above polymers of this invention involving as the essential steps:

(a) substituting lithium for halogen upon a ring carbon atom of a phenyl group, or for hydrogen on a ring carbon atom adjacent to ring nitrogen, in at least some of the aromatic rings of a polyphenylene, or a crosslinked styrene or vinylpyridine polymer or copolymer therebetween, crosslinked by a divinylarylene;

(b) contacting the resulting lithiated polymer with a di(hydrocarbyloxy)phenylarsine (formula PhAs(OR)$_2$) or with a trihydrocarbyloxyarsine (formula (RO)$_3$As) whereby the lithium substituent is replaced by an arsenical ester group, —AsPh(OR) or —As(OR)$_2$; R being any esterifying aliphatic, alicyclic or aromatic hydrocarbon (i.e. "hydrocarbyl").

We have found that oxidation reactions can be effected by hydrogen peroxide, generally under the conditions of the above noted prior art, but using our above described polymer substituted by arsenic groups as the catalyst. When the arsenic in such groups is trivalent, as in the above noted —AsPh(OR) and —As(OR)$_2$ groups, such trivalent arsenic becomes oxidized to pentavalent during use of the catalyst for oxidation by H$_2$O$_2$; and the above arsenical ester groups are hydrolyzed to form respectively a phenylarsono group (—As(Ph)(O)(OH)) and an arsono group (—As(O)(OH)$_2$). Conveniently, such oxidation and hydrolysis can be carried out on the material before using it as a catalyst, using H$_2$O$_2$ or other chemical oxidizing agent for such oxidation and hydrolysis.

Using our catalyst, open chain ketones can be oxidized to esters or a mixture of alcohol and carboxylic acid by H$_2$O$_2$, in the same general manner as disclosed in the above noted prior art. Likewise cyclic ketones in the presence of catalytic quantities of our polymers substituted by arsenic groups can be oxidized in aprotic solvents to lactones or to a mixture of lactones and hydroxy acids; or to alkyl hydroxyalkanoates, if primary alcohols are employed as the solvent. Arylalkyl ketones likewise react with H$_2$O$_2$ in the presence of catalytic quantities of these polymers substituted by arsenic groups to give phenyl carboxylates or a phenol and a carboxylic acid. Our catalyst can readily be separated in solid form from the product mixture in liquid form.

Our polymers substituted by arsenic groups have been found to be effective catalysts, also, for epoxidation of ethylenic double bonds by H$_2$O$_2$ generally as described in the above noted U.S. Pat. No. 3,993,673 to McMullen; and more especially, using a system of two liquid phases as described in more detail hereinafter.

DETAILED DESCRIPTION

Polymers of the Invention

Polymers substituted by arsenic groups particularly suitable for providing catalytic activity in the oxidation of dissolved organic substrates with hydrogen peroxide, in accordance with our invention, are polymers consisting essentially of a backbone of polymethylene in which one hydrogen atom on alternate carbon atoms is replaced by an aromatic group including particularly phenyl, 2-pyridyl, 3-pyridyl and/or 4-pyridyl groups. Preferably at least 10% of the aromatic groups are substituted by an arsenic group, particularly by an As (III) ester group especially a phenyl arsenite (—AsPh(OR)), or —As(OR)$_2$; and/or by an As (V) acid group, especially phenylarsono group —AsPh(O)(OH), or arsono group As(O)(OH)$_2$. The polymethylene backbones, moreover, are crosslinked by divinylbenzene ("DVB"). The degree of crosslinking is not critical; about 1% of DVB is sufficient to achieve the desired inertness and ruggedness while still allowing ready access of the reaction mixture to the catalytic sites.

Preparation of the Polymers of the Invention

Arsenic groups in the crosslinked polystyrene/DVB preferred for use in accordance with this invention can be introduced in the following way: Polystyrene/DVB porous particulates are brominated in broadly known manner, as a slurry in a solvent compatible with the polymer and inert under the reaction conditions to bromine, in contact with a bromination catalyst. Bromine is added in darkness and reacts at −10° to 50° C. with the slurried polymer. The brominated polymeric particulate is separated from the liquid reaction medium and then lithiated, for example using an alkyllithium dissolved in a suitable solvent. The resulting lithiated particulate is separated from the liquid reaction medium under inert conditions. The lithiated particulate is then reacted with a trivalent arsenic compound for example di(alkyloxy) phenyl arsine or arsine triethoxide, which then preferably is oxidized to convert the arsenic III compound to an arsenic V compound.

More particularly, the lithiation, and substitution of arsenic groups onto ring carbon, can be carried out by the following general procedure:

The washed and dried brominated polystyrene/DVB particulates are suspended in a suitable solvent such as benzene, toluene, dioxane, tetrahydrofuran, or diethyl ether and a molar excess such as 1 to 10 moles excess of a commercially available alkyllithium such as methyllithium or n-butyllithium is added under inert atmosphere at temperature between about −100 and −30° C. depending on the solvent used. The reaction mixture is then allowed to reach room temperature and to assure complete reaction, it may be maintained at room temperature or heated at from 30° C. to 80° C. for a period of between about 0.5 and 6 hours. Under inert atmosphere (N$_2$ or Ar or He), the lithiated polymer is filtered off, and is washed with an inert solvent such as above mentioned in order to remove the excess of alkyllithium.

A molar excess such as 1 to 10 moles excess of arsine trialkoxide dissolved in an inert solvent such as above mentioned is then added to the slurried lithiated polymer at temperatures of −10° to 40° C. and the mixture is then stirred for a period of about 2 to 30 hours at temperatures of +10° to +50° C. The resulting polymer particulates are then thoroughly washed with polar solvents such as acetonitrile, dioxane, tetrahydrofuran, or alcohol, in order to remove unreacted arsine trialkoxide.

The polymer then contains As (III) alkyl ester which is to be oxidized and hydrolyzed to the arsono group. This can be achieved by an aqueous oxidant solution such as 90 or 30% aqueous H$_2$O$_2$, a hypochlorite or hypochlorous acid, CrO$_2$Cl$_2$, or a complex of CrO$_3$ with pyridine; dissolved in an organic solvent miscible with water. The oxidation is carried out for a period of 0.1 to 6 hours at temperatures +10° to 70° C. The preferred oxidant is aqueous $H_2O_2$. The oxidized polymer is then thoroughly washed to remove the unreacted and reduced oxidant and then dried.

Alternatively, chlorinated or brominated polystyrene/DVB can be prepared from a mixture of styrene and chloro-or bromo-styrene, which can then be lithiated as just described. The copolymerization of the styrene, the chloro- or bromostyrene, and the DVB can be in suspension, initiated by conventional radical initiators such as benzoyl peroxide or azo-bis-isobutyronitrile.

Halostyrene/DVB polymers can be prepared similarly and lithiated similarly.

In the case of polymers containing pyridyl groups, their 2-position can be lithiated directly without a brominating step. The polymer is dispersed in a solvent such as benzene, toluene, dioxane, tetrahydrofuran, or diethyl ether together with an alkyllithium dissolved in the reaction mixture. The solvent to polymer weight ratio is between about 10 and 100:1. The reaction temperature is between about −30 and 50° C. depending on the solvent. The mole ratio of the polymer to the lithiating agent depends on the content of the pyridyl groups and is between about 2 and 20:1. The reaction time is between about 0.5 and 6 hours. The reaction generally requires stirring and inert atmosphere such as argon, nitrogen, helium and the like. The lithium replaces hydrogen on a ring carbon atom adjoining the ring nitrogen atom. Under some conditions the pyridyl nitrogen can be oxidized to the N-oxide by $H_2O_2$; but this reaction is minimized when the pyridyl ring is substituted by an arsenic group. Accordingly, it is desirable when the polymer contains pyridyl groups to lithiate substantially all of these groups, for subsequent replacement by arsenic groups.

Another polymer suitable for modification by arsenic groups is a lithiated polyphenylene described in the above cited U.S. Pat. No. 4,045,493.

Arsenic groups are introduced into the various lithiated polymers, described above, by reaction with arsenic derivatives, preferably trialkoxyarsine, and the product is then oxidized, essentially in the manner described above for lithiated polystyrene/DVB polymer obtained by lithiation of brominated polystyrene/DVB.

The concentration of arsenic groups in the polymer is controlled by the concentration of halogen substituent or of pyridyl groups in the polymer. This concentration or degree of substitution of the polymer with arsenic groups can be varied over a wide range; in general the activity of the catalyst varies correspondingly. As previously stated, polymers wherein at least about 10% of the aromatic rings contain the arsono group, —As(O)(OH)$_2$, as a substituent group are preferred for the purposes of this invention. These polymers are hereinafter sometimes called polymers "substituted by arsono groups."

Use of Polymers of the Invention as Catalyst of Ketone Oxidation

The ketone to be oxidized with hydrogen peroxide, in accordance with this invention, is preferably dissolved in a solvent such as acetonitrile or dioxane, at weight ratio of ketone to solvent up to about 10:1.

A polymer of this invention is then added to the ketone solution as oxidation catalyst at a ratio of mole equivalents of ketone:atom equivalents of arsenic in the catalyst between about 100:1 and 10:1; and preferably between about 100:1 and 20:1.

A solution of hydrogen peroxide is added to the ketone and catalyst. The relative concentration of ketone and hydrogen peroxide in the reaction is not critical. Initial molar ratios of ketone to hydrogen peroxide between about 1:1 and 6:1 will generally be used. An initial ratio between about 3:1 and 6:1 is desirable to assure a fast oxidation, a high efficiency in the use of hydrogen peroxide, and good selectivity in formation, from cyclic ketones, of lactones vs. hydroxy acids.

In the presence of water, e.g. if relatively dilute aqueous hydrogen peroxide is used (e.g. 30% aqueous $H_2O_2$), oxidation of cyclic ketones generally results not only in lactones but also in hydroxy acids. Moderate yields of lactone, however, are obtained even with 30% aqueous hydrogen peroxide if the ketone is employed in considerable excess over the hydrogen peroxide present (compare Table V). Good yields of lactones are obtained also when using relatively dilute aqueous $H_2O_2$, if a water-immiscible solvent is used, forming a two-phase system and using our catalyst, because as explained in more detail below, our catalyst is found to act as a "phase transfer" catalyst. If primary alcohols are employed as solvents, alkyl hydroxyalkanoates are formed exclusively; e.g. in methanol, cyclohexanone is oxidized to methyl 6-hydroxycaproate.

Ketones oxidizable in accordance with this invention include saturated aliphatic and alicyclic ketones. Unsaturated open chain and cyclic ketones can also be oxidized at the carbonyl group by our process. The oxidation of the double bond may also take place in such ketones, but these oxidations will not normally interfere with each other. Among the saturated ketones useful in the present invention are included alkanones with up to about 30 carbon atoms and cycloalkanones with up to about 20 carbon atoms; and their halogen and/or hydroxy substituted derivatives. Such ketones include cyclobutanone, cyclopentanone, cyclohexanone, 2-methylcyclohexanone, 2-phenylcyclohexanone, camphor, fenchone, 2-methylcyclopentanone, 2-phenylcyclopentanone, 2-chlorocyclohexanone, benzophenone, estrone and the like. Unsaturated ketones which can be oxidized at the carbonyl group by $H_2O_2$, using our polymer as catalyst, include alkenones with up to about 30 carbon atoms and cycloalkenones with up to about 20 carbon atoms and their halogen and/or hydroxy substituted derivatives. Such ketones include 3-cyclohexenone, 3-cyclopentenone, 4-methyl-3-cyclohexenone, 2-methyl-3-cyclohexenone, 2-phenyl-3-cyclohexenone. Preferred ketones for commercial applications include cyclohexanone, 2-methylcyclohexanone, cyclopentanone and polycyclic ketones such as estrone and other steroids for the formation of cyclic lactones.

Reaction solvents which can be used for the ketone oxidation include, but are not limited to, acetonitrile, diethyl ether, dioxane, tetrahydrofuran, propionitrile, methanol, chlorinated hydrocarbons, chloroform, and mixtures thereof.

The form of the hydrogen peroxide reactant is not critical. A preferred form is aqueous hydrogen peroxide, e.g. 30% to 90% by weight of hydrogen peroxide in water.

The reaction temperature is not critical, but a preferred range is 60° to 90° C. The reaction time depends on the reaction temperature. An internal standard can be used to determine the end of the reaction by chromatographic analysis. Internal standards include but are not limited to biphenyl.

Use of Polymers of the Invention as Catalyst of C=C Oxidation

As exemplified hereinbelow, ethylenically unsaturated substrates, such as specifically cyclohexene, cyclooctene, octene-1 and allyl alcohol can be oxidized by $H_2O_2$ using the catalyst of our invention under otherwise essentially the conditions for such oxidation known in the prior art. Moreover, as with water-insoluble ketones, our catalyst functions with water-insoluble unsaturated compounds as a "phase transfer" catalyst of oxidation.

Phase Transfer Catalysis of Oxidation

Our catalyst of crosslinked polystyrene substituted by arsono groups affords special advantage in oxidizing water-insoluble substrates, especially when the products are also water-insoluble. For such oxidations, our catalyst leads to non-hydrolyzed products even using relatively dilute aqueous hydrogen peroxide, such as 30% aqueous hydrogen peroxide, as oxidizing agent instead of the more costly concentrated $H_2O_2$. If the product is essentially water-insoluble, a non-hydrolyzed product is obtained in good yields by using an essentially water-immiscible solvent, such as a chlorinated hydrocarbon, e.g. chloroform. Our catalyst concentrates at the phase boundary between aqueous $H_2O_2$ solution and the solution of the compound to be oxidized. The arsono groups in the polymer are converted by contact with $H_2O_2$ in the aqueous phase to perarsono; and this group on contacting the oxidizable compound in the organic phase, oxidizes it with regeneration of the arsono group. Because the water-insoluble product remains almost entirely in the organic phase, it does not undergo hydrolysis to any serious extent. Thus, in this reaction of oxidation by $H_2O_2$ our catalyst, we have found, behaves as a "phase transfer catalyst". (See for a general overview of such processes, Angewandte Chemie, International Edition, Vol. 16, No. 8 (Aug. 1977) pp 493-558).

The catalyst can be separated from the liquid phases, e.g. by filtration, and reused; and the product phase can be separated, e.g. by decantation, from the aqueous phase.

If the oxidizable compound forms a somewhat water-soluble product, then the water solubility can be lowered by the well-known expedient of salting out, whereby to allow effective use of 30% aqueous $H_2O_2$ as oxidizing agent, as above described, in presence of our catalyst.

Illustrative of water-insoluble substrates oxidizable in water-immiscible solvents by dilute aqueous $H_2O_2$ in presence of our polymer, acting as a phase transfer catalyst, are polycyclic ketones such as 3-alkyl ethers of estrone, and $C_3$ and higher alkenes and cycloalkenes such as propene, the butenes, the hexenes, cyclohexene, cyclooctene and their higher homologues.

The Examples which follow are illustrative of our invention and set forth the best mode presently contemplated by us for carrying out the invention; but are not to be interpreted in a limiting sense.

INTRODUCING ARSENIC GROUPS ON POLYSTYRENE

EXAMPLE 1

(A) Preparation of Poly(p-bromostyrene)

In a typical bromination, 20 g of commercially available porous crosslinked polystyrene beads (Bio Beads, Bio Rad Labs, SX-1, 1% divinylbenzene, 14,000 mol wt. exclusion limit) and iron powder (1 g) were added to $CCl_4$ (100 ml) in a vessel wrapped with aluminum foil, to shut out light, and cooled to 0° in an ice bath. To this vigorously stirred slurry, a solution of $Br_2$ (4 g, 25 mmol) in $CCl_4$ (100 ml) was slowly added over a 3 hour period. The HBr gas, generated during the reaction, was allowed to escape into an aqueous $AgNO_3$ trap. The solution was left to stir overnight. Solvent was removed by filtration and the excess iron powder was removed from the beads with a magnet. The brominated polymer product was then washed successively in 500 ml each of 1:1 dioxane:concentrated HCl, 1:1 water:dioxane, water (twice), 1:1 water:5% ammonium hydroxide, water (twice), dioxane, toluene, and finally methanol. Each of these washings was done by stirring the polymer 15-30 minutes in the appropriate wash solution. This was followed by vacuum drying (25°, 0.1 Torr). Thorough removal of the metal and metal salt catalyst of bromination is advisable to avoid its catalyzing decomposition of hydrogen peroxide when the final polymer product is used to catalyze oxidation therewith. Analysis showed 8.14% Br; 84.80% C; 6.88% H. Such bromination of phenyl groups is broadly old and is known to result principally in para-substitution of phenyl groups by bromine.

(B) Conversion of Polymer of (A) to Polymer I (Polystyrene Substituted with Arsono Groups)

The brominated crosslinked polystyrene from above (5 g, 1.0 mmole of bromine/g, 8.14% Br) was suspended in 50 ml anhydrous tetrahydrofuran. After the solution had cooled to $-78°$ in an acetone-Dry Ice bath, 10 millimoles of commercial n-butyllithium as a 2.42 M solution in hexane was added slowly under argon. After the addition was complete, the mixture was allowed to warm to room temperature and stirring was continued for an additional 30 minutes. The solution was filtered and the lithiated polymer product was washed three times with fresh anhydrous tetrahydrofuran.

Arsine triethoxide (2.32 g, 11 mmoles) was then slowly added with a syringe under argon, to replace the lithium atom in the phenyl groups by arsenite ester group, $—As(OEt)_2$. The solution immediately changed from the orange color of the lithiated polymer to colorless. The solution was left stirring overnight. The resulting polymer substituted by arsenite groups, in the form of beads, was then washed three times with fresh anhydrous tetrahydrofuran. The beads were collected by filtration and washed with dioxane-water (1:1, twice), water (6 times), tetrahydrofuran-water (1:1 twice), tetrahydrofuran (3 times) and dry ether (3 times) to remove all remaining soluble arsenic compounds.

The As (III) of the arsenite groups in the phenyl rings was then oxidized to As (V) and hydrolyzed, using an $H_2O_2$ (90%)—$CH_3CN$ (1:5) volume mixture at 50° for 2 hours, whereby the arsenite groups were converted to arsono groups, $—AsO(OH)_2$. A painstaking analysis gave 4.36% As; 85.17% C; 7.07% H; 0.31% Br. This corresponds to substitution by arsono groups in 11% of the phenyl rings, and accounts for the whole of the composition (recognizing that the oxygen in the arsono group is in weight ratio of 64:100 with arsenic therein). Accordingly the only substituent on the aromatic rings, other than the arsono group, is a little bromine (which is highly stable toward $H_2O_2$).

EXAMPLE 2

(A) Preparation of Poly(p-bromostyrene) of High Bromine Content

In a typical bromination in which a high loading of bromine was desired, 30 g of the same crosslinked polystyrene beads used in Example I(A), together with $FeCl_3$ (2 g) were added to $CCl_4$ (100 ml) in a vessel wrapped with aluminum foil to shut out light. To this vigorously stirred slurry a solution of $Br_2$ (27 g, 168 mmole) in $CCl_4$ (100 ml) was added slowly over a 2 hour period. The solution was left to stir at room temperature for 72 hours. Solvent was removed by filtration and the solid brominated product was washed successively with acetone (500 ml in 50 ml portions), 1:1 dioxane: water (twice), dioxane, tetrahydrofuran, and finally diethyl ether. Each of these washings was done by stirring the product 15-30 minutes in the appropriate wash solution. This was followed by vacuum drying (25°, 0.1 Torr). Analyses: C, 64.20%; H. 5.29%; Br, 29.20%.

(B) Conversion of Polymer of (A) to Polymer II (Polystyrene Substituted With Arsono Groups)

The brominated crosslinked polystyrene from above (5 g, 3.7 mmole bromine/g, 29.2% Br) was suspended in 50 ml dry toluene. 145 mmoles commercial n-butyllithium as a 2.42 M solution in hexane was added under argon. The hexane was removed under vacuum and replaced with toluene. The solution of butyllithium was then added to the brominated polymer at −78° and then let warm to room temperature. It was then heated to 60° for 3 hours. The solvent was removed by filtration, the polymer was washed twice with 30 ml toluene, and 30 ml diethylether was added to the resulting lithiated polymer.

Arsine triethoxide (22 g, 104 mmoles) was then slowly added under argon and the solution was stirred overnight. The resin was then washed three times with anhydrous diethyl ether. The beads were collected by filtration and washed with 1:1 dioxane:water (300 ml), water (200 ml) and finally dioxane (200 ml). The As (III) was oxidized to As(V) and hydrolyzed with an $H_2O_2$ (90%)-$CH_3CN$ 1:5 volume ratio solution at 60° for about two hours. It was then washed with acetonitrile, water, dioxane, and finally diethyl ether. Analyses: C, 63%, H, 6.41%; As, 17.9%; Br, 0.45%. This corresponds to substitution by arsono groups of about 54% of the phenyl rings and accounts for the whole composition, when oxygen in the arsono groups is included.

KETONE OXIDATIONS CATALYZED BY POLYMER OF THE INVENTION

EXAMPLE 3

Insoluble 1% crosslinked polystyrene-divinylbenzene beads substituted by arsono groups (Polymer I or Polymer II respectively) were added to a solution of the ketone in acetonitrile or dioxane solvents. The ratio of the ketone (mmoles) to the catalyst (mmole of As) was varied from 170 to 20:1. A solution of $H_2O_2$ (90% or 30% aqueous) was then added; the mole ratio of ketone to $H_2O_2$ was varied from 1:1 to 6:1. The mixture was then heated to 80° and samples were withdrawn at intervals and analyzed by gc and nmr. The catalyst was filtered off, thoroughly washed with dioxane and diethyl ether, dried in vacuo, and recycled. All ratios in the tables below are mole ratios and % of a product is mole percent based on moles of $H_2O_2$ in the starting reaction mixture.

The results demonstrate repeated reuse of the polymer catalyst of this invention without substantial loss of arsenic content, as seen by retention of activity and by elemental analysis.

TABLE I

Oxidation of Cyclohexanone by $H_2O_2$ (1:1) in the Presence of Polystyrene Substituted by Arsono Groups (Polymer I, 4.3% As) in Acetonitrile Solvent

| Run No. | Time h. | Capro-lactone % | 6-Hydroxy-caproic Acid % | Comment |
|---|---|---|---|---|
| IA | 1.5 | 7 | — | First cycle of |
|  | 3 | 18 | — | the catalyst |
|  | 4.5 | 30 | — |  |
|  | 7 | 36 | — |  |
|  | 9 | 39 | 18.0 |  |
| IB | 2.5 | 11 | — | First recycle of |
|  | 4 | 22 | — | the catalyst |
|  | 6 | 24 | — |  |
| IC | 2 | 12 | none | Second recycle of |
|  | 4.5 | 21 | none | the catalyst |
|  | 6 | 26 | none |  |
| ID | 2 | 14 | — | Third recycle of |
|  | 4.5 | 29 | — | the catalyst |
|  | 6 | 37 | — |  |

Approx. 40:40:1 ketone:$H_2O_2$:As mole ratio; 90% aq. $H_2O_2$

TABLE II

Oxidation of 2-Methylcyclohexanone and Cyclohexanone by $H_2O_2$ (1:1) in the Presence of Polystyrene Substituted by Arsono Groups (Polymer I, 4.3% As) in Acetonitrile Solvent

| Run No. | Time h. | Lactone % | Hydroxy Acid % | Comment |
|---|---|---|---|---|
| 2-Methylcyclohexanone |  |  |  |  |
| IIA | 2 | 42.3 | — | First cycle |
|  | 4 | 58.5 | — | of the catalyst |
|  | 6 | 69.2 | — |  |
| IIB | 2 | 38.9 | none | First recycle of |
|  | 4 | 58.6 | none | the catalyst |
|  | 6 | 68.1 | none |  |
| Cyclohexanone |  |  |  |  |
| IIC | 2 | 13.4 | — | Second recycle of |
|  | 4 | 22.6 | — | the catalyst |
|  | 6 | 31.9 | 3.2 |  |
| 2-Methylcyclohexanone |  |  |  |  |
| IID | 2 | 40.2 | none | Third recycle of |
|  | 4 | 59.7 | none | the catalyst |
|  | 6 | 68.8 | none |  |

Approx. 36:36:1 ketone:$H_2O_2$:As mole ratio; 90% aq. $H_2O_2$

TABLE III

Elemental Analyses of Polymer I

| Element | 34700-1a catalyst when prepared | 34586-44a catalyst after 1st cycle | 34586-45 catalyst after 2nd cycle | 34586-46 catalyst after 3rd cycle | 34586-47 catalyst after 4th cycle |
|---|---|---|---|---|---|
| C | 85.17 | 84.08 | 84.30 | 85.89 | 82.87 |
| H | 7.07 | 7.12 | 7.18 | 7.65 | 7.49 |
| As | 4.36 | 4.24 | 3.76 | 4.28 | 3.92 |
| Br | 0.31 | — | — | — | — |

TABLE IV

Oxidation of Cyclohexanone by $H_2O_2$ in the Presence of Polystyrene Substituted by Arsono Groups (Polymer II, 17% As) in Dioxane Solvent

| Run No. | Time h. | Caprolactone % | 6-hydroxy-caproic acid % | Comment |
|---|---|---|---|---|
| IVA* | 1.5 | 11 | — | First cycle of the catalyst |
|  | 3 | 21 | — |  |
|  | 4.5 | 26 | — |  |
|  | 6.0 | 32 | — |  |
|  | 7.0 | 34 | 24 |  |
|  | 22.5 | 40 | 39 |  |
| IVB* | 2 | 19 | — | First recycle of the catalyst |
|  | 4 | 31 | — |  |
|  | 6 | 40 | 0 |  |
|  | 7.5 | 42 | 7 |  |
|  | 23 | 48 | 36 |  |
| IVC* | 1.7 | 15 | — | Second Recycle of the catalyst |
|  | 3 | 22 | — |  |
|  | 5.7 | 30 | — |  |
|  | 6.8 | 37 | 10 |  |
|  | 22 | 50 | 28 |  |
| IVD+ | 2 | 12 | — | Third recycle of the catalyst |
|  | 4 | 22 | — |  |
|  | 6 | 32 | — |  |
|  | 8 | 40 | — |  |
|  | 9.8 | 45 | — |  |
|  | 12 | 51 | — |  |
|  | 14 | 55 | — |  |
|  | 16 | 57 | 27 |  |

*Approx. 38:38:1 ketone:$H_2O_2$:As mole ratio
+ Approx. 51:26:1 ketone:$H_2O_2$:As mole ratio 90% aq. $H_2O_2$

TABLE V

Oxidation of Cyclohexanone by $H_2O_2$ in the Presence of Polystyrene Substituted by Arsono Groups (Polymer II, 17% As; 6:1 cyclohexanone:$H_2O_2$ Ratio) in Dioxane Solvent

| Run No. | Time h. | Caprolactone % | 6-hydroxy-caproic acid % |
|---|---|---|---|
| VA* | 1.5 | 9 | — |
|  | 3.5 | 15 | — |
|  | 5.8 | 24 | 4 |
|  | 7 | 37 | — |
|  | 10 | 39 | — |
|  | 13.3 | 43 | 20 |
|  | 30.5 | 28 | 63 |

*Approx. 180:30:1 ketone:$H_2O_2$:As mole ratio; 30% aq. $H_2O_2$

TABLE VI

Oxidation of Cyclic Ketones in the Presence of Polystyrene Substituted by Arsono Groups (Polymer II, 17% As; 5:1 ketone: $H_2O_2$ Ratio) in Dioxane Solvent

| Run No. | Time h. | Lactone % | hydroxy acid % |
|---|---|---|---|
| VIA* cyclohexanone | 1.7 | 32 | — |
|  | 3 | 46 | 0 |
|  | 3.8 | 51 | — |
|  | 4.5 | 56 | — |
|  | 5.3 | 58 | — |
|  | 6.6 | 62 | 12 |
|  | 9.5 | 64 | 15 |
|  | 12.8 | 62 | — |
| VIB* 2-methyl-cyclohexanone | 1 | 20 | — |
|  | 2 | 38 | 3 |
|  | 3.4 | 60 | 7 |
|  | 4.7 | 78 | 11 |
| VIC* cyclopentanone | 1 | 21 | — |
|  | 2.5 | 42 | — |
|  | 3.5 | 53 | — |
|  | 5 | 61 | — |
|  | 6.1 | 68 | — |
|  | 8 | 74 | — |
| VID* cyclobutanone | 1 | 99 | — |
| VIE* 2-phenylcyclohexanone | 1.5 | 42 | — |
|  | 2.5 | 67 | — |
| VIF+ estrone 3-methyl ether | 24 | 65 | — |
| VIG+ 2-methylcyclopentanone | 2.5 | 27 | — |
|  | 6 | 39 | — |
|  | 11 | 44 | — |
|  | 30 | 64 | 20 |

*Approx. 150:30:1 ketone:$H_2O_2$:As mole ratio
+ Approx. 30:30:1 ketone:$H_2O_2$:As mole ratio 90% aq. $H_2O_2$

TABLE VII

Oxidation of Acyclic Ketones in the Presence of Polystyrene Substituted by Arsono Groups (Polymer II, 17% As; 5:1 ketone:$H_2O_2$ Ratio) in Dioxane Solvent

| Run No. | Time h. | Ester % | Solvolysis Product % |
|---|---|---|---|
| VIIA* pinacolone | 4 | t-butyl acetate (35) | — |
|  | 9 | t-butyl acetate (57) | — |
|  | 25 | t-butyl acetate (83) | — |
| VIIB* acetophenone | 29 | phenylacetate (13) | — |

*approx. 150:30:1 ketone:$H_2O_2$:As mole ratio; 90% aq. $H_2O_2$

C=C OXIDATION CATALYZED BY POLYMER OF THE INVENTION

EXAMPLE 4

General Procedure

Insoluble crosslinked polystyrene-divinylbenzene beads substituted in phenyl rings by arsono groups (Polymer II of Example 2 (B) above with 17.9% As by analysis) were added to a solution of ethylenically unsaturated compound in dioxane solvent. A solution of $H_2O_2$ (90% aqueous in acetonitrile) was then added to the solution. A mole ratio of 150:30:1 olefin:$H_2O_2$:As in the polymeric catalyst was used.

The mixture was stirred in a 50 ml flask at 80° C.; samples were withdrawn periodically and analyzed by g.c., $H_2O_2$ titration, and $^1H$ nmr. The catalyst was ultimately filtered off, thoroughly washed with dioxane, dried in vacuo, and recycled.

The tablets below show the results obtained. In the tables, "%" designates mole percent yield of product based on moles of hydrogen peroxide in the starting reaction mixture. It will be noted from Table I that the recycled catalyst retained its original activity, indicating that no arsenic was lost in the process of catalyst use, recovery, and reuse through an initial cycle and four recyclings.

TABLE I

| Time Hours | Cyclohexane | | Comment |
|---|---|---|---|
|  | Cyclohexene Oxide (%) | Cyclohexane Diol (%) |  |
| 0.5 | 31 | 0 | First cycle of the catalyst |
| 2 | 57 | 7 |  |
| 5 | 63 | 17 |  |
| 7.5 | 60 | 27 |  |
| 0.5 | 21 | 0 | First recycle |
| 2 | 49 | 0 |  |

TABLE I-continued

| Time Hours | Cyclohexane Cyclohexene Oxide (%) | Cyclohexane Diol (%) | Comment |
|---|---|---|---|
| 5 | 69 | 5 | |
| 7.5 | 67 | 14 | |
| 0.5 | 24 | 0 | Second Recycle |
| 2 | 56 | 0 | |
| 3.5 | 69 | 2 | |
| 5 | 67 | 9 | |
| 7.5 | 65 | 22 | |
| 0.5 | 24 | 0 | Third Recycle |
| 2 | 55 | 0 | |
| 5 | 72 | 4 | |
| 7.5 | 70 | 14 | |
| 0.5 | 24 | 0 | Fourth Recycle |
| 2 | 57 | 0 | |
| 5 | 68 | 5 | |
| 7.5 | 67 | 19 | |

TABLE II

| | Allyl Alcohol | |
|---|---|---|
| Time Hours | Epoxide (%) | Diol (%) |
| 0.5 | 15 | 0 |
| 2 | 33 | 0 |
| 4 | 42 | 0 |
| 5 | 51 | 0 |
| 7 | 42 | 2 |

TABLE II

| | 1-Octene | |
|---|---|---|
| Time Hours | Epoxide (%) | Diol (%) |
| 0.5 | 3.5 | — |
| 2 | 10 | — |
| 5 | 20 | — |
| 7 | 24 | — |
| 10.5 | 30 | — |
| 14 | 35 | — |
| 21 | 37 | — |

C═C OXIDATION WITH TWO LIQUID PHASES PRESENT

EXAMPLE 5

Crosslinked polystyrene-divinylbenzene beads substituted in the phenyl rings by arsono groups (Polymer II of Example 2 (B) above, containing 0.25 mmole As) was added to a two phase system of 1.7 g of 30% aqueous $H_2O_2$ (15 mmoles of $H_2O_2$) and cyclooctene (7.5 mmoles) in chloroform (7 ml). The mixture was heated in a closed thick-walled tube at 70° C. for 45 hours. Cyclooctene oxide (6.7 mmol, 89% yield) was obtained after 45 hours. The polymer was then filtered and reused with no apparent loss of activity (90% yield after 55 hours at 70° C.).

KETONE OXIDATION WITH TWO LIQUID PHASES PRESENT

EXAMPLE 6

Crosslinked polystyrene-divinylbenzene substituted in the phenyl rings by arsono groups, in the form of beads (Polymer II of Example 2 (B) above) providing 0.13 mmole As was added to a two-phase system of 0.9 g of 30% aqueous $H_2O_2$ (7.8 mmoles of $H_2O_2$) and estrone-3-methylether (3.8 mmoles) in chloroform (5 ml). The mixture was heated in a closed thick-walled tube at 90° C. for 90 hours. The lactone of estrone-3-methylether (2.2 mmoles, 58% yield) was obtained after this time.

We claim:

1. An improved porous polymer in granular or bead form and useful for catalyzing oxidation by hydrogen peroxide, consisting essentially of phenyl or pyridyl groups, being linked together in polyphenylene, or pendant from a polymethylenic backbone which is crosslinked by a divinylarylene at least some of which phenyl or pyridyl groups are substituted on the ring by arsenic groups; wherein the improvement comprises freedom from nitrogenous and oxygen-containing substituents on the aromatic rings of said polymer thereby achieving high stability toward hydrogen peroxide, such that the polymer can be reused repeatedly to catalyze oxidation by hydrogen peroxide, and can be separated in solid form from the product mixture in liquid form, without substantial loss of arsenic content; and wherein the said arsenic groups are —AsPh(OR), —As(OR)$_2$, —AsPh(O) (OH), —As(O) (OH)$_2$ or a mixture thereof, "R" being hydrocarbyl.

2. Polymer of claim 1 having a polymethylenic backbone crosslinked by divinylbenzene and having phenyl or pyridyl groups pendant from alternate carbon atoms of the backbone.

3. Polymer of claim 2 wherein said pendant groups are phenyl and said arsenic groups are —As(OEt)$_2$ or —As(O) (OH)$_2$ or a mixture thereof, substituted into at least 10% of the phenyl groups.

4. Process for production of polymer in accordance with claim 1, comprising the steps of
   (a) substituting lithium for halogen upon a ring carbon atom of a phenyl group, or for hydrogen on a ring carbon atom adjacent to ring nitrogen, in at least some of the phenyl groups in a polyphenylene, or phenyl or pyridyl groups in a crosslinked styrene or vinylpyridine polymer or copolymer therebetween, crosslinked by a divinylarylene;
   (b) contacting the resulting lithiated polymer with a di(hydrocarbyloxy)phenylarsine or with a trihydrocarbyloxyarsine whereby the lithium substituent is replaced by the As(III) group —AsPh(OR) or —As(OR)$_2$.

5. Process of claim 4 wherein said As(III) group is oxidized to As(V) and is hydrolyzed to the phenylarsono group —AsPh(O) (OH) or to the arsono group —As(O) (OH)$_2$.

6. Process of claim 4 wherein said lithiated polymer formed in step (a) is derived from macroporous crosslinked polystyrene/DVB by brominating a slurry of said polystyrene/DVB in darkness in contact with a bromination catalyst at −10° to 50° C.; separating the resulting bromination product from the liquid reaction medium; lithiating a slurry of the resulting bromination product with excess alkyllithium under inert atmosphere at −100° to 80° C.; and separating the resulting lithiated polymer from the liquid reaction medium; and wherein to a slurry of the lithiated polymer, an excess of arsine trialkoxide is added and the slurry is maintained at −10° to 50°; the polymer obtained, containing As(III), is thoroughly washed with polar solvent to remove unreacted arsine trialkoxide; and the resulting polymer is subjected to oxidation with aqueous $H_2O_2$ at 10° to 70° C. to oxidize As(III) therein to As(V).

* * * * *